U S010973948B2

United States Patent
Hu et al.

(10) Patent No.: US 10,973,948 B2
(45) Date of Patent: *Apr. 13, 2021

(54) ABSORBABLE IRON-BASED DEVICE

(71) Applicant: Biotyx Medical (Shenzhen) Co., Ltd., Shenzhen (CN)

(72) Inventors: Jun Hu, Shenzhen (CN); Deyuan Zhang, Shenzhen (CN); Hongtao Sun, Shenzhen (CN); Liping Chen, Shenzhen (CN)

(73) Assignee: Biotyx Medical (Shenzhen) Co., Ltd, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/473,722

(22) PCT Filed: Dec. 19, 2017

(86) PCT No.: PCT/CN2017/117097
§ 371 (c)(1),
(2) Date: Jun. 26, 2019

(87) PCT Pub. No.: WO2018/121336
PCT Pub. Date: Jul. 5, 2018

(65) Prior Publication Data
US 2019/0381210 A1    Dec. 19, 2019

(30) Foreign Application Priority Data
Dec. 30, 2016  (CN) .......................... 201611264429.7

(51) Int. Cl.
| *A61L 31/02* | (2006.01) |
| *A61L 31/06* | (2006.01) |
| *A61L 31/14* | (2006.01) |
| *A61L 31/16* | (2006.01) |
| *A61L 17/00* | (2006.01) |
| *A61L 17/10* | (2006.01) |
| *A61L 17/12* | (2006.01) |
| *A61L 27/04* | (2006.01) |
| *A61L 27/34* | (2006.01) |
| *A61L 27/58* | (2006.01) |

(52) U.S. Cl.
CPC ............. *A61L 27/042* (2013.01); *A61L 27/34* (2013.01); *A61L 27/58* (2013.01); *A61L 31/022* (2013.01); *A61L 31/148* (2013.01); *A61L 31/16* (2013.01); *A61L 2300/418* (2013.01); *A61L 2300/42* (2013.01); *A61L 2400/18* (2013.01)

(58) Field of Classification Search
None
See application file for complete search history.

(56) References Cited

U.S. PATENT DOCUMENTS

| 2005/0209680 | A1 | 9/2005 | Gale et al. |
| 2012/0053678 | A1 | 3/2012 | Anand et al. |
| 2016/0279303 | A1 * | 9/2016 | Zhang ................... A61L 31/042 |

FOREIGN PATENT DOCUMENTS

| CN | 102228721 A | 11/2011 |
| CN | 104587534 A | 5/2015 |
| CN | 105597163 A | 5/2016 |
| WO | WO-2015062546 A1 * | 5/2015 | ........... A61L 31/042 |

OTHER PUBLICATIONS

International Search Report dated Mar. 23, 2018 in corresponding International application No. PCT/CN2017/117097; pp. 1-4.

* cited by examiner

*Primary Examiner* — Brian Gulledge
(74) *Attorney, Agent, or Firm* — Maier & Maier, PLLC

(57) ABSTRACT

An absorbable iron-based device includes an iron-based matrix and degradable polyester in contact with the surface of the iron-based matrix. The mass fraction of a low-molecular-weight part of the degradable polyester is less than or equal to 5%, and the molecular weight of the low-molecular-weight part is less than 10,000; or the mass fraction of a residual monomer in the degradable polyester is less than or equal to 2%.

17 Claims, 3 Drawing Sheets

ABSORBABLE IRON-BASED DEVICE

FIELD

The present application relates to an implantable medical device, and more particularly relates to an absorbable iron-based device.

BACKGROUND

As a vital element in a human body, iron takes part in numerous biochemical processes. An implantable device made of pure iron or an iron-based alloy may be gradually corroded and absorbed by human body after being implanted into human body, which is safer and more reliable and may effectively avoid long-term adverse reactions caused by long-time retention of a permanent implant in the human body, such as late restenosis, inflammatory reaction and failure of secondary intervention at the site where the implant is located.

The iron-based device is corroded slowly in an environment of an organism, and accelerated corrosion of the iron-based device may be realized by applying degradable polyester to its surface. The principle of accelerating the corrosion of the iron-based device with the use of a degradable polyester is that: in the early stage of an iron-based device containing degradable polyester implanted into the organism, soluble oligomers and residual monomers in the degradable polyester are released to form a local weak-acid environment around an iron-based substrate, thus accelerating localized corrosion of the iron-based substrate and degradation of the degradable polyester. In addition, a low molecular weight portion of the degradable polyester also may be degraded fast to a soluble oligomer or monomer, thus further accelerating the localized corrosion of the iron-based substrate and the degradation of the degradable polyester.

The corrosion of the iron-based device is not uniform because of the material composition, structure and size of the iron-based substrate, and loading stress. The iron-based device will generally complete endothelialization within one month after being implanted into a patient. So, it is clinically required that the device may at least keep an intact framework structure and have relatively high early mechanical properties within 1 month after implantation. Generally, the mild non-uniform corrosion of the iron-based device would not cause serious consequences, such as local fracture and collapse of a supporting structure, within one month after implantation. However, the degradable polyester applied to the surface of the iron-based device may increase the non-uniformity degree of the corrosion of the iron-based device, which possibly leads to local fracture of the iron-based device and affects the mechanical property of the iron-based device in the early stage after implantation. In addition, the non-uniform corrosion would cause corrosion products to accumulate locally around the iron-based device, and a biological abnormity would probably occur in the human tissue in contact with the site, which gives rise to a biological safety risk.

SUMMARY

In view of this, it is desirable to provide an absorbable iron-based device that improves the corrosion uniformity of the iron-based device in the early stage of implantation by applying a degradable polyester on the surface of or inside the iron-based substrate, thereby, minimizing the reduction of effectiveness and the biological safety risk which could be caused by the early non-uniform corrosion of the iron-based device.

The degrading process of a degradable polyester polymer is related to the content of residual monomers and molecular weight distribution in the degradable polyester. In the present application, the degrading process of the degradable polyester is controlled by adjusting the content of the residual monomer in the degradable polyester or the content of a low molecular weight portion in the degradable polyester, so as to improve the corrosion uniformity of the iron-based device in the early stage of implantation and lower the reduction of effectiveness of an implanted device and the biological safety risk which are caused by the early non-uniform corrosion of the iron-based device.

The present application provides an absorbable iron-based device, including an iron-based substrate and degradable polyester in contact with the surface of the iron-based substrate. The mass fraction of a low molecular weight portion in the degradable polyester is less than or equal to 5%, and the molecular weight of the low molecular weight portion is less than 10,000. Or, the mass fraction of the residual monomer in the degradable polyester is less than or equal to 2%.

In one embodiment, the mass fraction of the residual monomer is less than or equal to 1%.

In one embodiment, the mass fraction of the residual monomer is less than or equal to 0.1%. As the number of the monomers is much greater than that of the polymer under the same unit mass, and the monomer is ionized more easily than the polymer to produce acidic hydrogen ions, the mass fraction of the residual monomer in the degradable polyester has great influence on the early degradation of the degradable polyester. When the mass fraction of the residual monomer in the degradable polyester is less than or equal to 1%, the acidity around the iron-based device in the early stage may be effectively lowered so that the early corrosion of the iron-based device is more uniform.

A corrosion uniformity index is utilized to evaluate whether the corrosion of the iron-based device is uniform or not. A method to determine the corrosion uniformity index is described as below. After the iron-based device is corroded, action may be taken to uniformly cut an effective supporting portion of the iron-based device into i sections with equal axial lengths, wherein i is a natural number greater than or equal to 3. An effective supporting portion is in direct contact with a human tissue after the iron-based device is implanted into a human body. Next, detect the mass of iron element in the corrosion products attached to the surface of each section and also the mass of residual iron element in each section of the iron-based device, respectively. The sum of the two masses is the initial mass of the iron element of this section of iron-based device before corrosion. Then, calculate the ratio of the mass of the iron element in the corrosion product to the initial mass of the total iron element of this section of the iron-based device before corrosion, where there are i ratios in total. Next, define the standard deviation among the i ratios as the corrosion uniformity index of the iron-based device in this corrosion region. When the corrosion uniformity index is less than or equal to 30%, the iron-based device is corroded uniformly in this section. When the corrosion uniformity index is more than 30%, the iron-based device is not corroded uniformly in this section.

In one embodiment, the mass fraction of the low molecular weight portion is less than or equal to 2%. Since the low molecular weight portion in the degradable polyester is easily degraded into a soluble oligomer in the early stage of degradation, a reduction of the content of the low molecular weight portion in the degradable polyester could mitigate the acidity around the iron-based device in the early stage of degradation.

In one embodiment, the molecular weight of the low molecular weight portion is less than 100,000.

In one embodiment, the degradable polyester is obtained by separating and/or purifying a raw material of the degradable polyester through a precipitation method, a gel permeation chromatography, an ultrafiltration membrane filtration method or an extraction method.

In one embodiment, a ratio of the mass of the degradable polyester to the mass of the iron-based substrate is 1:(1 to 200). The ratio of the mass of the degradable polyester to the mass of the iron-based substrate is within this range, which ensures that the implanted iron-based device is degraded fast without remaining in the human body for a long time, and the long-term safety risk is lowered.

In one embodiment, the ratio of the mass of the degradable polyester to the mass of the iron-based substrate is 1:(6 to 100).

In one embodiment, the degradable polyester is at least one of polylactic acid, polyglycolic acid, polybutylene succinate, polyhydroxyalkanoate, polycaprolactone, polyethylene glycol adipate, a polylactic-co-glycolic acid or a polyhydroxybutyrate valerate copolymer. Or, the degradable polyester is formed by copolymerizing or physically blending of at least two monomers constituting polylactic acid, polyglycolic acid, polybutylene succinate, polyhydroxyalkanoate, polycaprolactone, polyethylene glycol adipate, polylactic-co-glycolic acid or polyhydroxybutyrate valerate copolymer.

In one embodiment, the degradable polyester is formed by copolymerizing or physically blending of at least one of the monomers constituting polylactic acid, polyglycolic acid, polybutylene succinate, polyhydroxyalkanoate, polycaprolactone, polyethylene glycol adipate, polylactic-co-glycolic acid or polyhydroxybutyrate valerate copolymer and at least one of the monomers constituting polyanhydride, poly (malate), starch, chitosan, cellulose, glycan or a derivative thereof.

In one embodiment, the degradable polyester is formed by copolymerizing or physically blending at least one monomer constituting a degradable polymer and at least one monomer constituting a nondegradable polymer. The nondegradable portion in the degradable polyester may mitigate the acidic environment around the iron-based device and delay the early corrosion of the iron-based device.

In one embodiment, the nondegradable polymer includes polyurethane, polycarbonate, polymethyl methacrylate, polystyrene, polybutylene or poly-n-butyl methacrylate.

The degradable polyester is in contact with the iron-based substrate in the form of a coating layer. The contact way between the coating layer and the iron-based substrate is at least one of the following manners: the coating layer at least partially covers the surface of the iron-based substrate; or the iron-based substrate is provided with gaps or grooves, and the coating layer is arranged in the gaps or in the grooves; or the iron-based substrate has an inner cavity, and the inner cavity is filled with the coating layer.

In one embodiment, the thickness of the coating layer is 2 to 100 microns. For example, the thickness of the coating layer may be 5 to 80 microns.

In one embodiment, the absorbable iron-based device further includes an active drug mixed with the degradable polyester. A ratio of the mass of the degradable polyester to the mass of the active drug is (0.2 to 20):1.

In one embodiment, the active drug is selected from the group consisting of: a drug for inhibiting vascular proliferation, an antiplatelet drug, an antithrombotic drug, an anti-inflammatory reaction drug or an antisensitization drug. The drug for inhibiting the vascular proliferation is selected from the group consisting of: taxol, a taxol derivative, sirolimus and a sirolimus derivative. The antiplatelet drug is cilostazol. The antithrombotic drug is heparin. The anti-inflammatory reaction drug is dexamethasone. The antisensitization drug is selected from the group consisting of diphenhydramine, chlorpheniramine, promethazine, hydrocortisone, triamcinolone, methylprednisolone, clarityne, fexofenadine, levocetirizine, mizolastine or ebastine.

In one embodiment, the iron-based device includes a vascular stent, a non-endovascular stent, an occluder, an orthopedic implant, a dental implant, a respiratory implant, a gynecological implant, an andrological implant, a suture or a bolt. The non-endovascular stent includes a tracheal stent, an esophageal stent, a urethral stent, an intestinal stent or a biliary stent. The orthopedic implant comprises a fixing screw, a fixing rivet or a bone plate.

Compared with the prior art, the present application at least the following beneficial effects. In the absorbable iron-based device of the present application, the degradable polyester is applied onto the surface of the iron-based substrate. The absorbable iron-based device is corroded more uniformly in the early stage of implantation by controlling the mass fraction of the residual monomers of the degradable polyester applied to the surface of the iron-based substrate or the mass fraction of the low molecular weight portion of the degradable polyester. Meanwhile, the absorbable iron-based device would not produce a number of degradation products within short time during corrosion in the early stage of implantation. Therefore, the reduction of the effectiveness of the implanted device or the biological safety risk caused by the fast and non-uniform corrosion of the iron-based device in the early stage of implantation may be effectively prevented, and then the possibility of injury to the human body is reduced.

BRIEF DESCRIPTION OF THE DRAWINGS

FIG. 1a is a pathological section staining diagram zoomed in by 25 times under a microscope, FIG. 1b is a pathological section staining diagram zoomed in by 100 times under the microscope, FIG. 1c is a pathological section staining diagram zoomed in by 200 times under the microscope;

FIG. 3a is a pathological section staining diagram zoomed in by 25 times under the microscope, FIG. 3b is a pathological section staining diagram zoomed in by 100 times under the microscope, and FIG. 3c is a pathological section staining diagram zoomed in by 200 times under the microscope.

DETAILED DESCRIPTION OF THE EMBODIMENTS

Figure 1A:
FIGS. 1a to 1c are pathological section staining diagrams of tissues around a stent of Embodiment 1 after the stent is implanted into an abdominal aorta of a New Zealand rabbit for 3 days.

First, a detection method of degradable polyester and an iron-based device which are related to the present application is described below.

Detection Method of the Mass of the Degradable Polyester

The mass of the degradable polyester is measured through the following method: weighing the total mass $M_0$ of an iron-based device, removing the degradable polyester from the surface of the iron-based substrate with a good solvent for the degradable polyester, then weighing the mass $M_{iron}$ of the iron-based substrate, and obtaining the mass ($M_0$-$M_{iron}$) of the degradable polyester of the iron-based device by a difference value method.

Detection Method of the Mass Fraction of the Residual Monomers in the Degradable Polyester The mass fraction of the residual monomers in the degradable polyester=the mass $M_{monomer}$ of the residual monomer/the mass ($M_0$-$M_{iron}$) of the degradable polyester×100%.

The mass $M_{monomer}$ of the residual monomers is detected by a gas chromatographic method.

Detection conditions are as follows:

An Agilent 7820A type gas chromatograph of the Agilent Technologies is used. A chromatographic column CD-ACID WAX (size: 30 m×0.32 mm, 0.50 micron) of, for example, Shanghai ANPEL is used. Column temperature and heating conditions: the column is heated from about 50° C. to 180° C. at a heating rate of about 20° C./min, and the temperature is kept steady for 5 min; and then the column is heated from about 180° C. to 200° C. at a heating rate of 10° C./min, and the temperature is kept steady for 6.5 min. A sample injection chamber works at 200° C. A detector works at 250° C. The column flow velocity is 1.8 mL/min. The diversion ratio is 2:1. The make-up gas is 25 mL/min. The hydrogen flow is 30 mL/min. The air flow is 300 mL/min.

Detection Method of the Weight-Average Molecular Weight, Diffusion Coefficient and Molecular Weight Distribution of the Degradable Polyester The weight-average molecular weight, the diffusion coefficient and the molecular weight distribution of the degradable polyester are detected by using of a GPC-multiangle laser light scattering spectrometer combined with a molecular weight test system of, for example, the Wyatt Company, USA. The test system includes a liquid phase pump and a sample injector provided by, for example, Agilent Technologies, an Agilent PL MIXED-C type GPC column (size: 7.5×300 mm, 5 microns) of the Agilent Technologies, and a multiangle laser light scattering spectrometer and a differential detector of the Wyatt Company. Detection conditions are as follows: a flowing phase: tetrahydrofuran; a pump flow velocity: 1 mL/min; a sample injection amount: 100 uL; a laser wavelength: 663.9 nm; and test temperature: 35° C.

Detection Method of the Corrosion Uniformity of the Iron-Based Device

The corrosion uniformity of the iron-based device is estimated according to a corrosion uniformity index. The corrosion uniformity index K can be detected by an in-vitro test method, detected by the following steps: the iron-based device is put into a sample bottle capable of immersing the iron-based device at the minimum volume, and normal saline is added to just completely immerse the iron-based device; the sample bottle is placed into a constant-temperature water bath environment at 36.5° C. to 37.5° C. and oscillated at a rate of 40 to 80 r/min. The iron-based device is taken out at a predetermined observation time point, such as on the 3rd day or the 7th day, an effective supporting portion of the iron-based device is uniformly cut into i sections with equal axial lengths, wherein i is a natural number which is bigger than or equal to 3, and the effective supporting portion is in direct contact with human tissue after the iron-based device is implanted into the human body, for example, the effective supporting portion of a regularly shaped vascular stent is the whole vascular stent, and the effective supporting portion of a blood vessel filter is a middle section which does not include filter nets at two ends and is used for supporting a blood vessel. Then, the i sections of iron-based devices are respectively put into corresponding tartaric acid solutions with a mass concentration of 3% for ultrasonic treatment, and corrosion products attached to the surfaces of the i sections of iron-based devices are enabled to respectively fall into the corresponding i tartaric acid solutions; at the end of the ultrasonic treatment, each section of the iron-based devices is respectively dried and weighed to obtain the masses $m_1$, $m_2$, $m_3$ ... $m_i$, of the total i sections of the iron-based devices; the tartaric acid solutions corresponding to the i sections of iron-based devices are respectively dissolved by concentrated nitric acid and respectively digested in a microwave digestion system till the total i parts of the mixed solutions are obtained, wherein at the moment, all the corrosion products are converted into detectable dissolved states. Distilled water is respectively added into the i parts of the mixed solutions to fix the volumes at $V_1$, $V_2$, $V_3$ ... $V_i$, and concentrations $C_1$, $C_2$, $C_3$ ... $C_i$ of iron ion of the i parts of volume-fixed mixed solutions are respectively detected by an atomic absorption spectrometry method; according to $M_i=C_i\times V_i$, the masses $M_1$, $M_2$, $M_3$ ... $M_i$ of the iron element in the i parts of the volume-fixed mixed solutions are respectively calculated, namely the masses of the iron element in the corrosion products produced by the i sections of iron-based devices during corrosion. Therefore, the initial mass of the iron element of each of the i sections of iron-based devices before corrosion is $m_i+M_i$ and then according to $P_i=M_i/(m_i+M_i)\times 100\%$, a ratio $P_1$, $P_2$, $P_3$ ... $P_1$ of the mass of the iron element in the corrosion product to the initial mass of the iron element of this section of the iron-based device before corrosion is obtained, and there are i ratios in total. A standard deviation among $P_1$, $P_2$, $P_3$ ... $P_i$ is the corrosion uniformity index of the iron-based device within this section. When the corrosion uniformity index is less than or equal to 30%, it is considered that the iron-based device is corroded uniformly within this section. When the corrosion uniformity index is more than 30%, it is considered that the iron-based device is not corroded uniformly within this section.

Detection conditions of the atomic absorption spectrometry method are as follows: a 240FS type atomic absorption spectrometer of, for example, the Agilent Company, USA; a detection wavelength: 248.3 nm; a gap: 0.2 mm; combustion-supporting gas: acetylene; and a flow velocity of the combustion-supporting gas: 2.0 L/min.

The corrosion uniformity index K also may be detected by an animal implantation test method. In particular, the absorbable iron-based device is implanted into the body of an animal, then the corroded iron-based device is taken out at a predetermined observation time point, and the effective supporting portion of the iron-based device is uniformly cut into i sections with equal axial lengths so as to detect the corrosion uniformity index K.

Biological Safety Risk Evaluation Method of the Iron-Based Device

The biological safety risk is an abnormal phenomenon such as inflammatory reaction, cytotoxicity, sensitization, thrombosis or hemolysis in a biological tissue or an organism caused by the implanted iron-based device. An animal implantation test is carried out to check whether the corrosion products produced by the early corrosion of the iron-based device pose the biological safety risk to peripheral tissues of the animal, including the following steps: the iron-based device is implanted into a tissue (such as a coronary artery, an abdominal aorta, an iliac artery and an inferior vena cava) in the body of a small mammal (such as a rabbit, a dog or a pig); and then the iron-based device and its adjacent tissue are taken out at a predetermined observation time point such as on the 7th day and the 28th day, to observe corrosion situations on the appearance and the inner wall of the iron-based device to judge whether there are corrosion products accumulated or not, whether severe local corrosion occurs or not and whether a biological morphological abnormality (such as inflammatory reaction, thrombi and decaying) occurs in the adjacent tissue of the iron-based device or not.

It should be further noted that the degradable polyester used in the technical solution of the present application may be a commercially available commodity meeting the requirement for the mass fraction of the low molecular weight portion or the mass fraction of the residual monomer, and also may be a sample prepared by those skilled in the art through separation and/or purification of a commercially available degradable polyester raw material.

Separation and Purification Methods of the Degradable Polyester

In the present application, the polyester raw material may be separated and/or purified through the following four methods, thus obtaining the degradable polyester used in exemplary Embodiments 1 to 11. However, the separation and/or purification methods of the degradable polyester are not limited to the following methods. The degradable polyester obtained by separating and/or purifying the degradable polyester raw material through any method may be applied to the absorbable iron-based device of the present application as long as the mass fraction of the low molecular weight portion or the residual monomer of the degradable polyester meets the requirement of the technical solution of the present application.

A precipitation method includes the following steps: the degradable polyester raw material is dissolved into a good solvent (such as ethyl acetate, tetrahydrofuran, acetone, dichloromethane and chloroform) for the degradable polyester to obtain a degradable polyester solution; then a poor solvent (such as methanol, ethanol, isopropanol and water), serving as a precipitant, is added into the degradable polyester solution and uniformly mixed with it, and at the moment, precipitates appear in the mixed degradable polyester solution; liquid in the degradable polyester solution is poured out after the solution is placed for some time, and the precipitates was retained; and the precipitates are repeatedly precipitated twice or three times by the same method, and the finally obtained precipitates are dried to obtain the degradable polyester used in the absorbable iron-based device of the present application. Gel permeation chromatography (GPC for short) includes the following steps: the degradable polyester raw material is dissolved into a good solvent (such as ethyl acetate, tetrahydrofuran, acetone, dichloromethane or chloroform) for the degradable polyester to obtain the degradable polyester solution; the degradable polyester solution is injected into a GPC column (such as a PL MIXED-C type GPC preparation column of the Agilent) through a liquid phase sample injection pump, and the degradable polyester in the degradable polyester solution flows out in sequence according to the molecular weights from large to small after passing through the GPC column; and the effluent is retained for a certain period of time, and then dried to obtain the degradable polyester used in the absorbable iron-based device of the present application.

An ultrafiltration membrane filtration method includes the following steps: the degradable polyester raw material is dissolved into a good solvent (such as ethyl acetate, tetrahydrofuran, acetone, dichloromethane or chloroform) for the polyester to obtain the degradable polyester solution; the degradable polyester solution is pressurized and enabled to pass through an ultrafiltration membrane; at the moment, most of the residual monomers and the low molecular weight portion in the degradable polyester and the solvent may pass through the ultrafiltration membrane, and a high molecular weight portion and a little of the residual monomers and low molecular weight portion are retained on the surface of the ultrafiltration membrane; and the residues retained on the surface of the ultrafiltration membrane are dried to obtain the degradable polyester used in the absorbable iron-based device of the present application.

An extraction method includes the following steps: the degradable polyester raw material is immersed in a poor solvent (such as water, methanol, ethanol and isopropanol) for the degradable polyester, and the degradable polyester is taken out after certain time and then dried to obtain the degradable polyester used in the absorbable iron-based device of the present application.

To clearly understand the objectives, technical solutions and advantages of the present application, the technical solution of the present application is further described below in detail with specific embodiments. It should be understood that the specific embodiments described herein are merely explanatory of the present application, but not intended to limit the present application.

Unless otherwise defined, all technical and scientific terms used herein are the same as meanings of general understandings of those skilled in the art of the present application. The terms used in the description of the text are only used to describe the specific embodiments, but not intended to limit the present application.

Embodiment 1

Polylactic acid was separated and purified through a GPC method, so as to obtain polylactic acid containing a residual monomer at a mass fraction of 0.1%. The polylactic acid containing the residual monomer at the mass fraction of 0.1% was dissolved in ethyl acetate, and the mixture was sprayed onto the surface of an iron alloy-based vascular stent with a carbon content of 2.11 wt. %, so as to obtain a degradable polyester coated iron-based alloy vascular stent of Embodiment 1. In the degradable polyester coated iron alloy-based vascular stent of the present embodiment, the average thickness of the degradable polyester coating layer is 5 microns. A ratio of the mass of the degradable polyester to the mass of the iron-based substrate is 1:80.

Three identical stents were made by using the same raw materials and method, and one stent was randomly put into a sample bottle, and normal saline was added into the sample bottle to just completely immerse the stent. The sample bottle was kept in a constant-temperature water bath at 36.5 to 37.5° C. and oscillated at a rate of 40 to 80 r/min. The stent was taken out on the 3rd day. The corroded stent was uniformly cut into three sections with equal axial lengths. A ratio of the mass of the iron element in the corrosion products of each section to the initial mass of the iron element of this section of the stent before corrosion was measured according to the above-mentioned method, and there were 3 ratios in total. A standard deviation among the 3 ratios was calculated. The standard deviation is a corrosion uniformity index of the stent provided by the present embodiment. The test shows that the corrosion uniformity index of the stent provided by Embodiment 1 is 16.6% after the stent is immersed in the normal saline for 3 days.

Figure 1B:
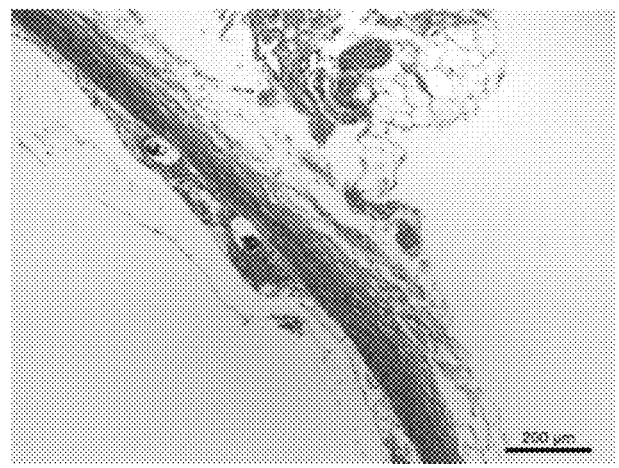
Figure 1C:
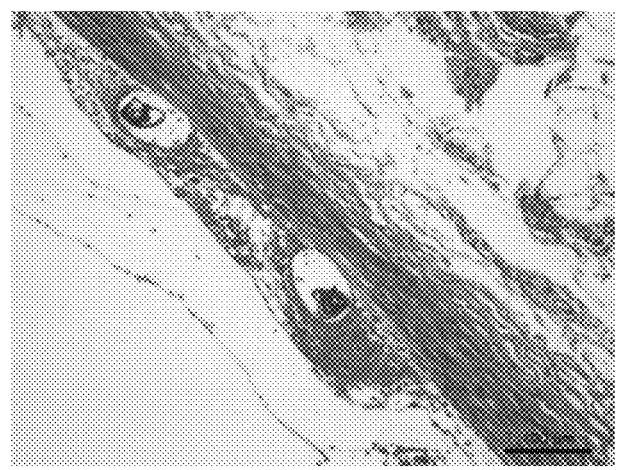

The other two stents were implanted into the abdominal aortas of two New Zealand rabbits with the same weight, sex and age, respectively. The two stents with its adjacent vascular tissues were retrieved on the 3rd day and on the 28th day post-operation, respectively. The stent with the vascular tissue was cut open and flattened along the axial direction to observe the integrity of the stent with a microscope and to observe whether any severe local corrosion or any severe accumulation of corrosion products occurs on the outer or inner surfaces of the stent and whether a biological morphological abnormality occurs in the peripheral tissue of the stent or not. The adjacent tissue of the stent implanted for 3 days was subjected to pathological analysis. Tissue section staining images are shown in FIG. 1a to 1c.

The result shows that when the stent provided by the present embodiment is implanted for 3 days, no fracture occurs on the appearance of the stent, and no severe local corrosion or severe accumulation of corrosion products occurs on the outer and inner surfaces of the stent. It can be seen from FIGS. 1a to 1c that when the stent provided by the present embodiment is implanted for 3 days, no biological morphological abnormality occurs in the adjacent tissue of the stent. When the stent is implanted for 28 days, no supporting strut of the stent is broken, no severe local corrosion or severe accumulation of corrosion products occur on the outer and inner surfaces of the stent, and there is no biological morphological abnormality in the adjacent tissue of the stent.

Embodiment 2

Polylactic acid was separated and purified by a GPC method, so as to obtain polylactic acid in which the mass fraction of a low molecular weight portion with a molecular weight less than 100,000 is 2% and the mass fraction of the residual monomers is 1.0%. The obtained polylactic acid was dissolved in ethyl acetate, and the mixture was sprayed onto the surface of a pure iron stent, so as to obtain a degradable polyester coated pure iron stent of Embodiment 2. In the present embodiment, the average thickness of the degradable polyester coating layer is 5 microns. A ratio of the mass of the degradable polyester to the mass of the iron-based substrate is 1:100.

Figure 2:
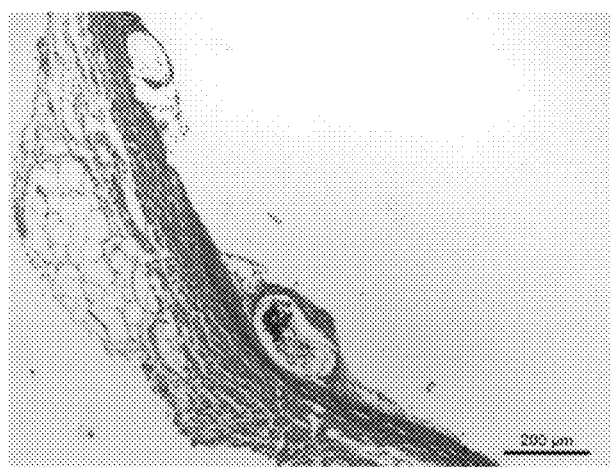
FIG. 2 is a pathological section staining diagram of the tissue around a stent of Embodiment 2 after the stent is implanted into the abdominal aorta of the New Zealand rabbit for 7 days.

The degradable polyester coated pure iron stent provided by Embodiment 2 was implanted into the abdominal aorta of a New Zealand rabbit. The stent with its adjacent vascular tissue was retrieved on the 7th day after implantation. The stent with the vascular tissue was cut open and flattened along the axial direction to observe the morphological integrity of the stent with a microscope and to observe whether any severe local corrosion or severe accumulation of corrosion products occurs on the outer and inner surfaces of the stent and whether a biological morphological abnormality occurs in the adjacent tissue of the stent. The adjacent tissue of the stent was subjected to pathological analysis. A tissue section staining image is as shown in FIG. 2.

The result shows that when the stent provided by the present embodiment is implanted for 7 days, no supporting strut of the stent is broken, and no severe local corrosion or severe accumulation of corrosion products occurs on the outer and inner surfaces of the stent. It can be seen from FIG. 2 that when the stent provided by the present embodiment is implanted for 3 days, no biological morphological abnormality occurs in the adjacent tissue of the stent. According to the above-mentioned measurement method of the corrosion uniformity index, the corrosion uniformity index of the stent provided by Embodiment 2 is measured to be 5.4% when the stent is implanted for 7 days.

Embodiment 3

Polylactic acid was separated and purified by an ultrafiltration membrane filtration method, so as to obtain polylactic acid in which the mass fraction of the residual monomers is 0.05%. The obtained polylactic acid was dissolved in ethyl acetate, and the mixture was sprayed onto the surface of an iron alloy-based stent, so as to obtain a degradable polyester coated iron alloy-based stent of Embodiment 3. In the present embodiment, the average thickness of the degradable polyester coating layer is 2 microns. The ratio of the mass of the degradable polyester to the mass of the iron-based substrate is 1:200.

The degradable polyester coated iron alloy-based stent provided by Embodiment 3 was implanted into the abdominal aorta of a New Zealand rabbit. The stent with adjacent vascular tissue was retrieved on the 7th day after implantation. The stent with the vascular tissue was cut open and flattened along the axial direction to observe the integrity of the stent with a microscope and to observe whether any severe local corrosion or severe accumulation of corrosion products occurs on the outer and inner surfaces of the stent, and whether a biological morphological abnormality occurs in the adjacent tissue of the stent.

The result shows that when the stent provided by the present embodiment is implanted for 7 days, no supporting strut of the stent is broken, no severe local corrosion or severe accumulation of corrosion products occurs on outer and inner surfaces of the stent, and no biological morphological abnormality occurs in the adjacent tissue of the stent.

According to the above-mentioned measurement method of the corrosion uniformity index, the corrosion uniformity index of the stent provided by Embodiment 3 is measured to be 6.8% when the stent is implanted for 7 days.

Embodiment 4

Polycaprolactone in which the mass fraction of the low molecular weight portion with a molecular weight less than 10,000 was dissolved in ethyl acetate, and the mixture was sprayed onto the surface of a pure iron stent, so as to obtain a degradable polyester coated pure iron stent of Embodiment 4. In the present embodiment, the average thickness of the degradable polyester coating layer is 2 microns. A ratio of the mass of the degradable polyester to the mass of the iron-based substrate is 1:200.

The degradable polyester coated pure iron stent provided by Embodiment 4 was implanted into the abdominal aorta of a New Zealand rabbit. The stent and its adjacent vascular tissue were retrieved on the 7th day after implantation. The stent with the vascular tissue was cut open and flattened along the axial direction to observe the morphological integrity of the stent with a microscope and to observe whether any severe local corrosion or severe accumulation of corrosion products occurs on the outer and inner surfaces of the stent and whether a biological morphological abnormality occurs in the adjacent tissue of the stent.

The result shows that when the stent provided by the present embodiment is implanted for 7 days, no supporting strut of the stent is broken, no severe local corrosion or severe accumulation of corrosion products occurs on the outer and inner surfaces of the stent, and no biological morphological abnormality occurs in the adjacent tissue of the stent.

According to the above-mentioned measurement method of the corrosion uniformity index, the corrosion uniformity index of the stent provided by Embodiment 4 is measured to be 14.4% when the stent is implanted for 7 days.

Embodiment 5

Polylactic acid was separated and purified by a precipitation method, so as to obtain polylactic acid in which the mass fraction of the residual monomers is 0.1% and the mass fraction of the low molecular weight portion with a molecular weight less than 100,000 is 1.1%. The obtained polylactic acid and sirolimus were mixed at a mass ratio of 2:1 and then dissolved in ethyl acetate, and the mixture solution was sprayed onto the surface of an iron alloy-based stent, so as to obtain a degradable polyester coated iron alloy-based stent of Embodiment 5. In the present embodiment, the average thickness of the degradable polyester coating layer is 80 microns. A ratio of the mass of the degradable polyester to the mass of the iron-based substrate is 1:3.

Two identical iron alloy-based stents provided by Embodiment 5 were fabricated with the same raw materials and method. They were implanted into the abdominal aortas of two New Zealand rabbits with the same weight, sex and age, respectively. The stents with adjacent vascular tissues were retrieved on the 7th day and the 28th day after implantation, respectively. The stent with the vascular tissue was cut open and flattened along the axial direction to observe the appearance integrity of the stent with a microscope and to observe whether any severe local corrosion or severe accumulation of corrosion products occurs on the outer and inner surfaces of the stent and whether a biological morphological abnormality occurs in the adjacent tissue of the stent.

The result shows that when the stent provided by the present embodiment is implanted for 7 days, no supporting strut of the stent is broken, no severe local corrosion or severe accumulation of corrosion products occurs on the outer and inner surfaces of the stent, and no biological morphological abnormality occurs in the adjacent tissue of the stent. When the stent is implanted for 28 days, no supporting strut of the stent is broken, no severe local corrosion or severe accumulation of corrosion products occurs on the outer and inner surfaces of the stent, and no biological morphological abnormality occurs in the adjacent tissue of the stent.

According to the above-mentioned measurement method of the corrosion uniformity index, the corrosion uniformity indexes were measured when the stents provided by Embodiment 5 were implanted for 7 days and 28 days, respectively. The test shows that the corrosion uniformity index of the stent provided by Embodiment 5 is measured to be 7.7% after the stent is implanted for 7 days, and the corrosion uniformity index of the stent provided by Embodiment 5 is measured to be 16.1% after the stent is implanted for 28 days.

Embodiment 6

A polylactic-co-glycolic acid was separated and purified by an extraction method, so as to obtain a polylactic-co-glycolic acid containing residual monomers at a mass fraction of 2%. The optimized polylactic-co-glycolic acid, taxol and dexamethasone were mixed at a mass ratio of 4:1:1 and dissolved in ethyl acetate, and the mixture was sprayed onto the surface of an iron alloy-based stent, so as to obtain a degradable polyester coated iron alloy-based stent of Embodiment 6. In the present embodiment, the average thickness of the degradable polyester coating layer is 10 microns. A ratio of the mass of the degradable polyester to the mass of the iron-based substrate is 1:30.

The degradable polyester coated iron alloy-based stent provided by Embodiment 6 was implanted into the abdominal aorta of a New Zealand rabbit. The stent and its peripheral vascular tissue were retrieved on the 7th day after implantation. The stent with the vascular tissue was cut open and flattened along the axial direction to observe the appearance integrity of the stent with a microscope and to observe whether any severe local corrosion or severe accumulation of corrosion products occurs on the outer and inner surfaces of the stent and whether a biological morphological abnormality occurs in the adjacent tissue of the stent.

The result shows that when the stent provided by the present embodiment is implanted for 7 days, no supporting strut of the stent is broken, no severe local corrosion or severe accumulation of corrosion products occurs on the outer and inner surfaces of the stent, and no biological morphological abnormality occurs in the adjacent tissue of the stent.

According to the above-mentioned measurement method of the corrosion uniformity index, the corrosion uniformity index of the stent provided by Embodiment 6 is measured to be 5.4% when the stent is implanted for 7 days.

Embodiment 7

Polylactic acid was separated and purified by an ultrafiltration membrane filtration method, so as to obtain polylactic acid containing a low molecular weight portion with a molecular weight less than 100,000 at a mass fraction of 3.5%. A blend obtained by blending the obtained polylactic acid with chitosan at a mass ratio of 1:1, the blend was mixed with heparin and cilostazol at a mass ratio of 8:1:1 and dissolved in ethyl acetate, and the mixture was sprayed onto the surface of an iron alloy-based stent, so as to obtain a degradable polyester coated iron alloy-based stent of Embodiment 7. In the present embodiment, the average thickness of the degradable polyester coating layer is 4 microns. A ratio of the mass of the degradable polyester to the mass of the iron-based substrate is 1:100.

The degradable polyester coated iron alloy-based stent provided by Embodiment 7 was implanted into the abdominal aorta of a New Zealand rabbit. The stent with adjacent vascular tissue was retrieved on the 7th day after implantation. The stent with the vascular tissue was cut open and flattened along the axial direction to observe the appearance integrity of the stent with a microscope and observe whether any severe local corrosion or severe accumulation of corrosion products occurs on the outer and inner surfaces of the stent and whether a biological morphological abnormality occurs in the adjacent tissue of the stent.

The result shows that when the stent provided by the present embodiment is implanted for 7 days, no supporting strut of the stent is broken, no severe local corrosion or severe accumulation of corrosion products occurs on the outer and inner surfaces of the stent, and no biological morphological abnormality occurs in the adjacent tissue of the stent.

According to the above-mentioned measurement method of the corrosion uniformity index, the corrosion uniformity index of the stent provided by Embodiment 7 is measured to be 3.9% when the stent is implanted for 7 days.

Embodiment 8

Polyglycolic acid was separated and purified by a GPC method, so as to obtain polyglycolic acid containing the residual monomers at a mass fraction of 2%. The obtained polyglycolic acid and clarityne were mixed at a mass ratio of 0.2:1 and dissolved in acetone, and the mixture was sprayed onto the surface of an iron alloy-based stent with a carbon content of 0.5%, so as to obtain a degradable polyester coated iron alloy-based stent of Embodiment 8. In the present embodiment, the average thickness of the degradable polyester coating layer is 12 microns. A ratio of the mass of the degradable polyester to the mass of the iron-based substrate is 1:20.

The degradable polyester coated iron alloy-based stent provided by Embodiment 8 was implanted into the abdominal aorta of a New Zealand rabbit. The stent and its peripheral vascular tissue were retrieved on the 7th day after implantation. The stent with the vascular tissue was cut open and flattened along the axial direction to observe the appearance integrity of the stent with a microscope and observe whether any severe local corrosion or severe accumulation of corrosion products occurs on the outer and inner surfaces of the stent and whether a biological morphological abnormality occurs in the peripheral tissue of the stent.

The result shows that when the stent provided by the present embodiment is implanted for 7 days, no supporting strut of the stent is broken, no severe local corrosion or severe accumulation of corrosion products occurs on the outer and inner surfaces of the stent, and no biological morphological abnormality occurs in the peripheral tissue of the stent.

According to the above-mentioned measurement method of the corrosion uniformity index, the corrosion uniformity index of the stent provided by Embodiment 8 is measured to be 9.9% when the stent is implanted for 7 days.

Embodiment 9

Commercially available polycaprolactone and polycarbonate were blended at a mass ratio of 2:1 to obtain a blend, and it was measured that the mass fraction of a low molecular weight portion of the blend with a molecular weight less than 10,000 is 2%. The blend and hydrocortisone were mixed at a mass ratio of 20:1 and dissolved in ethyl acetate, and the mixture was sprayed onto the surface of an iron alloy-based stent, so as to obtain a degradable polyester coated iron alloy-based stent of Embodiment 9. In the present embodiment, the average thickness of the degradable polyester coating layer is 8 microns. A ratio of the mass of the degradable polyester to the mass of the iron-based substrate is 1:30. The degradable polyester coated iron alloy-based stent provided by Embodiment 9 was implanted into the abdominal aorta of a New Zealand rabbit. The stent and its adjacent vascular tissue were retrieved on the 7th day after implantation. The stent with the vascular tissue was cut open and flattened along the axial direction to observe the appearance integrity of the stent with a microscope and to observe whether any severe local corrosion or severe accumulation of corrosion products occurs on the outer and inner surfaces of the stent and whether a biological morphological abnormality occurs in the adjacent tissue of the stent.

The result shows that when the stent provided by the present embodiment is implanted for 7 days, no supporting strut of the stent is broken, no severe local corrosion or severe accumulation of corrosion products occurs on the outer and inner surfaces of the stent, and no biological morphological abnormality occurs in the adjacent tissue of the stent.

According to the above-mentioned measurement method of the corrosion uniformity index, the corrosion uniformity index of the stent provided by Embodiment 9 is measured to be 8.1% when the stent is implanted for 7 days.

Embodiment 10

Poly-dl-lactic acid was separated and purified by a GPC method, so as to obtain poly-dl-lactic acid in which the mass fraction of the low molecular weight portion with a molecular weight less than 100,000 is 0.5% and the mass fraction of the residual monomers is 1.5%. The obtained poly-dl-lactic acid was mixed with sirolimus at a mass ratio of 9:1 and dissolved in ethyl acetate, and the mixture was sprayed onto the surface of an iron alloy-based stent, so as to obtain a degradable polyester coated iron alloy-based stent of Embodiment 10. In the present embodiment, the average thickness of the degradable polyester coating layer is 100 microns. A ratio of the mass of the degradable polyester to the mass of the iron-based substrate is 1:1.

The degradable polyester coated iron alloy-based stent provided by Embodiment 10 was implanted into the abdominal aorta of a New Zealand rabbit. The stent and its peripheral vascular tissue were retrieved on the 7th day after implantation. The stent with the vascular tissue was cut open and flattened along the axial direction to observe the appearance integrity of the stent with a microscope and observe whether any severe local corrosion or severe accumulation of corrosion products occurs on the outer and inner surfaces of the stent and whether a biological morphological abnormality occurs in the adjacent tissue of the stent.

The result shows that when the stent provided by the present embodiment is implanted for 7 days, no supporting strut of the stent is broken, no severe local corrosion or severe accumulation of corrosion products occurs on the outer and inner surfaces of the stent, and no biological morphological abnormality occurs in the adjacent tissue of the stent.

According to the above-mentioned measurement method of the corrosion uniformity index, the corrosion uniformity index of the stent provided by Embodiment 10 is measured to be 17.1% when the stent is implanted for 7 days.

Embodiment 11

Polybutylene succinate was separated and purified by a precipitation method, so as to obtain polybutylene succinate in which the mass fraction of the low molecular weight portion with a molecular weight less than 100,000 is 2% and the mass fraction of the residual monomers is 0.5%. The obtained polybutylene succinate and promethazine were mixed at a mass ratio of 4:1 and dissolved in ethyl acetate, and the mixture was sprayed onto the surface of an iron alloy-based stent, so as to obtain a degradable polyester coated iron alloy-based stent of Embodiment 11. In the present embodiment, the average thickness of the degradable polyester coating layer is 40 microns. A ratio of the mass of the degradable polyester to the mass of the iron-based substrate is 1:6.

The degradable polyester coated iron alloy-based stent provided by Embodiment 11 was implanted into the abdominal aorta of a New Zealand rabbit. The stent and its peripheral vascular tissue were retrieved on the 7th day after implantation. The stent with the vascular tissue was cut open and flattened along the axial direction to observe the appearance integrity of the stent with a microscope and observe whether any severe local corrosion or severe accumulation of corrosion products occurs on the outer and inner surfaces of the stent and whether a biological morphological abnormality occurs in the peripheral tissue of the stent.

The result shows that when the stent provided by the present embodiment is implanted for 7 days, no supporting strut of the stent is broken, no severe local corrosion or severe accumulation of corrosion products occurs on the outer and inner surfaces of the stent, and no biological morphological abnormality occurs in the peripheral tissue of the stent.

According to the above-mentioned measurement method of the corrosion uniformity index, the corrosion uniformity index of the stent provided by Embodiment 11 is measured to be 28.8% when the stent is implanted for 7 days.

Contrast 1

Polylactic acid in which the content of residual monomers is 2.2% and the mass fraction of the low molecular weight portion with a molecular weight less than 10,000 is 10.9% was dissolved in ethyl acetate, and the mixture was sprayed onto the surface of an iron alloy-based vascular stent with a carbon content of 2.11 wt. %, so as to obtain a degradable polyester coated iron alloy-based vascular stent of Contrast 1. In the degradable polyester coated iron alloy-based vascular stent of Contrast 1, the average thickness of the degradable polyester coating layer is 5 microns. A ratio of the mass of the degradable polyester to the mass of the iron-based substrate is 1:80.

Figure 3A:
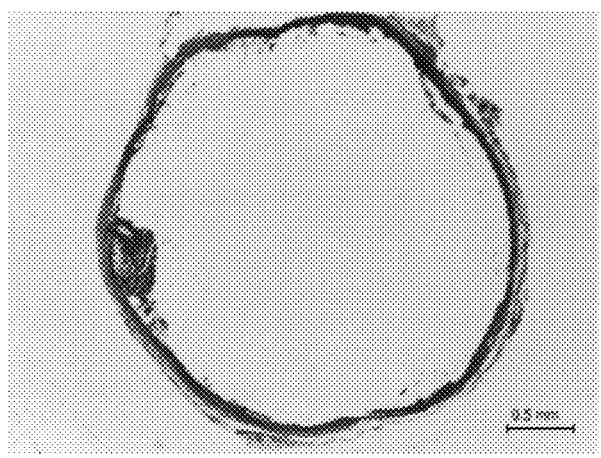
FIGS. 3a to 3c are pathological section staining diagrams of tissues around a stent of Contrast 1 after the stent is implanted into the abdominal aorta of a New Zealand rabbit for 3 days.
Figure 3B:
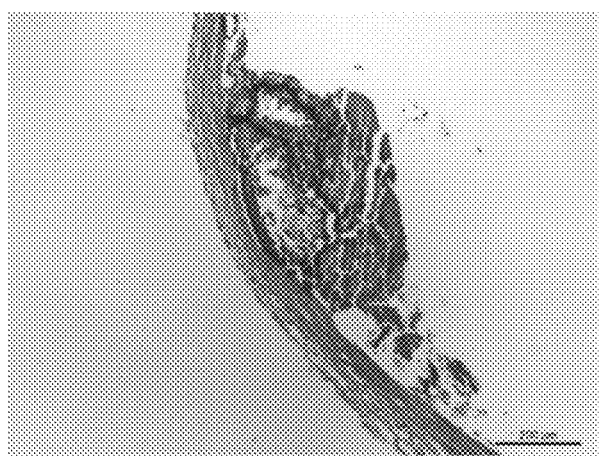
Figure 3C:
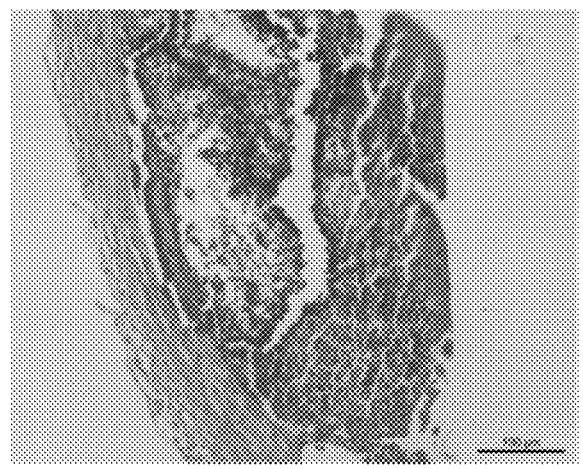

Two stents which are the same as the degradable polyester coated iron alloy-based vascular stent of Contrast 1 were made by using the same raw materials and method. They were implanted into the abdominal aortas of two New Zealand rabbits with the same weight, sex and age, respectively. The two stents with adjacent vascular tissues were retrieved on the 3rd day and the 28th day after implantation, respectively. The stent with the vascular tissue was cut open and flattened along the axial direction to observe the appearance integrity of the stent with a microscope and observe whether any severe local corrosion or severe accumulation of corrosion products occurs on the outer and inner surfaces of the stent and whether a biological morphological abnormality occurs in the peripheral tissue of the stent. The peripheral tissue of the stent implanted for 3 days was subjected to tissue pathological analysis. Staining pathologic section images are as shown in FIGS. 3a to 3c.

The result shows that when the stent of Contrast 1 is implanted for 3 days, severe local corrosion occurs on the inner surface of the stent, and a number of corrosion products are accumulated in the severely locally corroded region on the inner surface of the stent. It can be seen from FIGS. 3a to 3c that a thrombus appears in the peripheral tissue of the stent. When the stent of Contrast 1 is implanted for 28 days, severe local corrosion occurs on both the outer and inner surfaces of the stent, and some supporting struts are broken, which severely affects the overall supporting force of the stent. In addition, a number of corrosion products are accumulated in the severely locally corroded regions on both the outer and inner surfaces of the stent, and some thrombi could be observed adjacent to the stent. According to the above-mentioned measurement method of the corrosion uniformity index, the corrosion uniformity indexes were detected when the stent of Contrast 1 was implanted for 3 days and 28 days, respectively. The test shows that the corrosion uniformity index of the stent of Contrast 1 is measured to be 32.3% when the stent is implanted for 3 days, and the corrosion uniformity index of the stent of Contrast 1 is measured to be 33.6% when the stent is implanted for 28 days.

Compared with the stent provided by Embodiment 2, the stent of Contrast 1 is different in that the mass fractions of the residual monomers and the low molecular weight portion of the degradable polyester applied to the surface of the stent are relatively high, which leads to a great and fast corrosion of the degradable polyester in the early stage of implantation, so that the stent substrate corroded fast and non-uniform corrosion occurred in the early stage of implantation, and produced a number of corrosion products within a short period, resulting in the reduction of the effectiveness of the stent and raising the biological safety risks, such as thrombosis.

In conclusion, in the absorbable iron-based devices of the present application, the degradable polyester is applied onto the surface of the iron-based substrate. The absorbable iron-based device provided by the present application is corroded more uniformly in the early stage by controlling the mass fraction of the residual monomers of the degradable polyester applied to the surface of the iron-based substrate or by controlling the mass fraction of the low molecular weight portion of the degradable polyester. Meanwhile, the absorbable iron-based device would not produce too many corrosion products within a short period of time during corrosion in the early stage of implantation. Therefore, the absorbable iron-based devices provided by the present application may effectively prevent the reduction of the effectiveness or the biological safety risks caused due to the fast and non-uniform corrosion of the iron-based device in the early stage of implantation, and reduce the possibility of injury to a human body.

It should be noted that in Embodiments 1 to 11, the specific implementation modes of the present application are schematically described only in the situation that the iron-based substrate was fully covered by the degradable polyester. It can be understood that the degradable polyester may also partially cover the surface of the iron-based substrate. It can be understood that when the iron-based substrate is provided with gaps or grooves, the degradable polyester may be applied into the gaps or the grooves. It can be further understood that when the iron-based substrate has an inner cavity, the inner cavity can be filled with the degradable polyester.

It should be further noted that in Embodiments 1 to 11, the specific implementation modes of the present application are schematically described only through the vascular stent. The technical solutions provided by the present application also may be applied to other implantable devices, such as: other lumen stents (such as a tracheal stent, an esophageal stent, a urethral stent, an intestinal stent or a biliary stent), other cardiovascular implants (such as a heart occluder, a vascular filter and a vascular plug), an orthopedic implant (such as a fixing screw, a fixing rivet or a bone plate), a gynecological implant, an andrological implant, a respiratory implant, a dental implant, a suture or a bolt.

The above contents describe the embodiments of the present application, but the present application is not limited to the above-mentioned specific implementation modes. The above-mentioned specific implementation modes are only for schematic purposes, but not intend to restrict the application. Those ordinarily skilled in the art can further make many forms under the inspiration of the present application without departing from the purpose of the present application and the scope of claims, and these forms shall all fall within the protection of the present application.

The invention claimed is:

1. An absorbable iron-based device, comprising: an iron-based substrate and degradable polyester in contact with a surface of the iron-based substrate, wherein the mass fraction of a low molecular weight portion in the degradable polyester is less than or equal to 5% and the molecular weight of the low molecular weight portion is less than 100,000;
   wherein optionally the mass fraction of one or more residual monomers in the degradable polyester is less than or equal to 2%;
   and wherein the degradable polyester is at least one of polylactic acid, polyglycolic acid, polybutylene succinate, polyhydroxyalkanoate, polycaprolactone, polyethylene glycol adipate, a polylactic-co-glycolic acid or a polyhydroxybutyrate valerate copolymer; or, the degradable polyester is formed by copolymerizing or physically blending at least two of the monomers constituting the polylactic acid, the polyglycolic acid, the polybutylene succinate, the polyhydroxyalkanoate, the polycaprolactone, the polyethylene glycol adipate, the polylactic-co-glycolic acid or the polyhydroxybutyrate valerate copolymer.

2. The absorbable iron-based device according to claim 1, wherein the mass fraction of the one or more residual monomers is less than or equal to 1%.

3. The absorbable iron-based device according to claim 1, wherein the mass fraction of the one or more residual monomers is less than or equal to 0.1%.

4. The absorbable iron-based device according to claim 1, wherein the mass fraction of the low molecular weight portion is less than or equal to 2%.

5. The absorbable iron-based device according to claim 1, wherein the molecular weight of the low molecular weight portion is less than 10,000.

6. The absorbable iron-based device according to claim 1, wherein the degradable polyester is obtained by separating and/or purifying a raw material of the degradable polyester through a precipitation method, a gel permeation chromatography, an ultrafiltration membrane filtration method or an extraction method.

7. The absorbable iron-based device according to claim 1, wherein a ratio of the mass of the degradable polyester to the mass of the iron-based substrate is 1:(1 to 200).

8. The absorbable iron-based device according to claim 1, wherein the ratio of the mass of the degradable polyester to the mass of the iron-based substrate is 1:(6 to 100).

9. The absorbable iron-based device according to claim 1, wherein the degradable polyester is formed by copolymerizing or physically blending at least one of the monomers constituting the polylactic acid, the polyglycolic acid, the polybutylene succinate, the polyhydroxyalkanoate, the polycaprolactone, the polyethylene glycol adipate, the polylactic-co-glycolic acid or the polyhydroxybutyrate valerate copolymer and at least one of the monomers constituting polyanhydride, poly(malate), starch, chitosan, cellulose, glycan or a derivative thereof.

10. The absorbable iron-based device according to claim 1, wherein the degradable polyester is formed by copolymerizing or physically blending at least one monomer constituting a degradable polymer and at least one monomer constituting a nondegradable polymer.

11. The absorbable iron-based device according to claim 10, wherein the nondegradable polymer comprises polyurethane, polycarbonate, polymethyl methacrylate, polystyrene, polybutylene or poly-n-butyl methacrylate.

12. The absorbable iron-based device according to claim 1, wherein the degradable polyester is in contact with the iron-based substrate in the form of a coating layer; and the contact way between the coating layer and the iron-based substrate is at least one of the following: the coating layer at least partially covers the surface of the iron-based substrate; or the iron-based substrate is provided with gaps or grooves, and the coating layer is arranged in the gaps or the grooves; or the iron-based substrate has an inner cavity, and the inner cavity is filled with the coating layer.

13. The absorbable iron-based device according to claim 12, wherein the thickness of the coating layer is 2 to 100 microns.

14. The absorbable iron-based device according to claim 13, wherein the thickness of the coating layer is 5 to 80 microns.

15. The absorbable iron-based device according to claim 1, wherein the absorbable iron-based device further comprises an active drug mixed with the degradable polyester; and a ratio of the mass of the degradable polyester to the mass of the active drug is (0.2 to 20):1.

16. The absorbable iron-based device according to claim 15, wherein the active drug is selected from the group consisting of a drug for inhibiting vascular proliferation, an antiplatelet drug, an antithrombotic drug, an anti-inflammatory reaction drug or an antisensitization drug; the drug for inhibiting the vascular proliferation is selected from the group consisting of taxol, a taxol derivative, sirolimus or a sirolimus derivative; the antiplatelet drug is cilostazol; the antithrombotic drug is heparin; the anti-inflammatory reaction drug is dexamethasone; and the antisensitization drug is selected from the group consisting of diphenhydramine, chlorpheniramine, promethazine, hydrocortisone, triamcinolone, methylprednisolone, clarityne, fexofenadine, levocetirizine, mizolastine or ebastine.

17. The absorbable iron-based device according to claim 1, wherein the iron-based device comprises a vascular stent, a non-endovascular stent, an occluder, an orthopedic implant, a dental implant, a respiratory implant, a gynecological implant, an andrological implant, a suture or a bolt; the non-endovascular stent comprises a tracheal stent, an esophageal stent, a urethral stent, an intestinal stent or a biliary stent; and the orthopedic implant comprises a fixing screw, a fixing rivet or a bone plate.

* * * * *